United States Patent [19]  [11] 4,289,784
Bochis et al. [45] Sep. 15, 1981

[54] PYROMELLITIC DIIMIDES AND METHOD OF INCREASING FEED EFFICIENCY IN RUMINANT ANIMALS

[75] Inventors: Richard J. Bochis, East Brunswick; Michael H. Fisher; Bruce O. Linn, both of Bridgewater, all of N.J.

[73] Assignee: Merck & Co., Inc., N.J.

[21] Appl. No.: 142,795

[22] Filed: Apr. 22, 1980

Related U.S. Application Data

[62] Division of Ser. No. 954,040, Oct. 23, 1978, abandoned.

[51] Int. Cl.³ .................... A61K 31/40; C07D 209/56
[52] U.S. Cl. ................................ 424/274; 260/326 C
[58] Field of Search ................... 260/326 C; 424/274

[56] References Cited

U.S. PATENT DOCUMENTS

| | | | |
|---|---|---|---|
| 3,078,228 | 2/1963 | Smith et al. | 260/326 C |
| 3,624,212 | 11/1971 | Hennart | 424/274 |
| 3,738,840 | 6/1973 | Anderson | 96/100 |
| 3,931,224 | 1/1976 | Santa et al. | 260/326 C |

FOREIGN PATENT DOCUMENTS 1157503 7/1969 United Kingdom.
1173943 12/1969 United Kingdom.
1181020 7/1970 United Kingdom.

OTHER PUBLICATIONS

Chem. Abstracts 88:194117d (1978); 84:150376a; 43982y; 13504b (1976); 83:59699b; 82:87103a (1975); 79:19700f (1973); 77:48850u; 76:72279q; 33987x (1972); 75:89332d; 75:63340e; 74:55134m (1971); 71:81122g; 61062j; 70:38694n (1969); 69:97581a; 43899s; 68:59326t; 59329w (1968); 67:116726d (1967); 65:13620f (1966); 63:4435f (1965); 60:4054g (1964); 59:372c (1963).
S. Gitis et al., Zhurnal Organicheskoi Khimii, vol. 2, No. 7, pp. 1265-1267 (1966) Eng. translation, Derivatives of the Diimide of Pyromellitic Acid.

Primary Examiner—Donald G. Daus
Assistant Examiner—M. C. Eakin
Attorney, Agent, or Firm—David L. Rose; Harry E. Westlake

[57] ABSTRACT

Novel substituted pyromellitic diimides are disclosed wherein the compounds are assymetrically substituted with a variety of substituent groups. Processes for the preparation of such compounds are also disclosed. The novel assymetrically substituted pyromellitic diimides are useful for administration to ruminant animals to increase feed efficiency, shift volatile fatty acid production in the ruminants from acetate with an increase in the more energetically efficient propionate and butyrate and to suppress methane formation in the rumen. Composition and methods of treatment utilizing said compounds as the active ingredient thereof are also disclosed.

13 Claims, No Drawings

PYROMELLITIC DIIMIDES AND METHOD OF INCREASING FEED EFFICIENCY IN RUMINANT ANIMALS

This is a division, of application Ser. No. 954,040, filed Oct. 23, 1978 now abandoned.

SUMMARY OF THE INVENTION

The novel compounds of this invention are described as substituted pyromellitic diimides wherein the two imide nitrogen atoms are assymetrically substituted. Thus, it is an object of this invention to describe such compounds. A further object of this invention is to describe processes for the preparation of such compounds. A still further object is to describe the use of such compound for the administration to ruminant animals in order to increase feed efficiency, to shift the production of volatile fatty acids away from acetate with an increase in propionate and butyrate, and to suppress methane formation. Further objects will become apparent from a reading of the following description.

DESCRIPTION OF THE INVENTION

The novel assymetically substituted pyromellitic diimides of this invention are best described in the following structural formula:

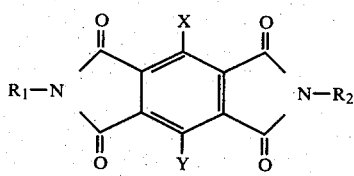

(I)

wherein $R_1$ and $R_2$ are not the same and represent hydrogen, loweralkyl, loweralkenyl, loweralknyl, cycloalkyl, loweralkanoyl, benzoyl, substituted phenyl wherein the substituent is sulfonamido, hydroxy, carboxy, nitro, methylthio, or hydroxy loweralkyl; substituted loweralkyl wherein the substituents are one or two of hydroxy, halogen, nitro, loweralkoxy, carboxy, phenyl, hydroxyloweralkoxy, loweralkanoyloxy, phenoxy, amino, mono- or di-loweralkylamino, mercapto, loweralkylthio, loweralkylsulfinyl, loweralkylsulfonyl, loweralkoxycarbonyl, loweralkoxycarbonyl, carbamyl, hydroxyloweralkylthio, hydroxyloweralkylsulfinyl, hydroxyloweralkylsulfonyl, hydroxyloweralkylamino, di-(hydroxyloweralkyl)amino, loweralkanoylamino or hydroxyphenyl; diloweralkylamino, or mono-substituted amino wherein the substituent is loweralkanoyl, benzoyl or loweralkoxycarbonyl; and X and Y are independently hydrogen, loweralkyl or halogen.

In the instant application the term "loweralkyl" is intended to include those alkyl groups containing from 1 to 6 carbon atoms in either a straight or branched configuration. Exemplary of such alkyl groups are a methyl, ethyl, propyl, isopropyl, butyl, tert-butyl, pentyl, hexyl, and the like.

The term "loweralkenyl" is intended to include those alkenyl groups containing a single unsaturation in a straight or branched chain length of from 2 to 6 carbon atoms. Exemplary are the groups ethenyl, propenyl, butenyl, pentenyl, hexenyl and the like.

The term "loweralkynyl" is intended to include those alkynyl groups containing one triple bond in a straight or branched claim of from 2-6 carbon atoms. Exemplary are the groups, ethynyl, propynyl, butynyl, pentynyl, hexynyl, and the like.

The term "cycloalkyl" is intended to include those cyclic alkyl groups containing from 3 to 6 carbon atoms exemplified by cyclopropyl, cyclobutyl, cyclopentyl and cyclohexyl.

The term "loweralkanoyl" is intended to include those alkanoyl groups of straight or branched configuration containing from 2 to 6 carbon atoms exemplified by acetyl, propionyl, butyryl, isobutyryl, pentanoyl, hexanoyl and the like.

The term "loweralkanoyloxy" is intended to include the foregoing loweralkanoyl groups bonded to the loweralkyl pyromellitic diimide substrate through an oxygen atom.

The term "loweralkoxy" is intended to include those alkoxy groups containing from 1 to 6 carbon atoms in either a straight or branched configuration, exemplified by methoxy, ethoxy, propoxy, isopropoxy, butoxy, tert-butoxy, pentoxy, hexoxy and the like.

The term "loweralkoxycarbonyl" is intended to include the foregoing alkoxy groups bonded to the pyromellitic diimide substrate through a carbonyl group.

The preferred compounds of this invention are realized in the foregoing structural formula wherein $R_1$ and $R_2$ are not the same and are hydrogen, loweralkyl, loweralkenyl, substituted loweralkyl wherein the substituent are one or two of hydroxy, amino, mono- or di-loweralkylamino, loweralkoxy, carboxy, carbamyl, phenyl, hydroxyloweralkoxy, hydroxyloweralkylthio, loweralkanoyloxy, mercapto, loweralkylthio, loweralkylsulfinyl, loweralkylsulfonyl, loweralkoxycarbonyl; loweralkanoyl, diloweralkylamino, benzoylamino, and X and Y are hydrogen.

More preferred compounds of this invention are realized when in the above formula $R_1$ and $R_2$ are not the same and are hydrogen, loweralkyl, loweralkenyl, substituted loweralkyl wherein the substituent is one of hydroxy or loweralkanoyloxy, loweralkylthio, loweralkylsulfinyl, loweralkylsulfonyl, hydroxyloweralkylthio, hydroxyloweralkoxy; loweralkanoyl or diloweralkylamino.

The most preferred compounds of this invention are those where $R_1$ and $R_2$ are hydrogen, loweralkyl, substituted loweralkyl wherein the substituent is one of hydroxy, hydroxyloweralkoxy, or hydroxyloweralkylthio.

The compounds of the instant invention are prepared by processes outlined in the following reaction scheme:

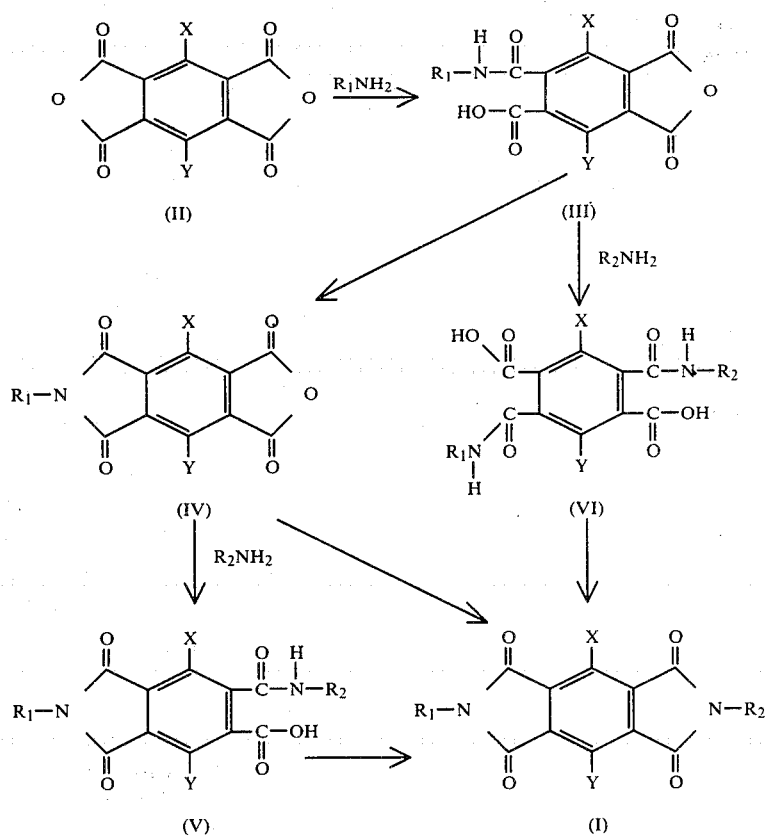

In the foregoing reaction scheme $R_1$ and $R_2$ are as defined above.

The preparation of the compound of this invention begins with pyromellitic dianhydride (II) which is treated with a substituted amine (represented by $R_1NH_2$, however, the order of reaction is not dependent upon which amine is employed and either the $R_1$ or $R_2$ amine could be reacted first. The reaction is carried out in an aprotic solvent such as acetone, tetrahydrofuran, dimethylformamide, dimethyl acetamide, diphenyl ether, dioxane, and the like, and is complete in about 5 minutes to 2 hours. A single molar equivalent of the amine is employed. The reaction is preferably maintained in an anhydrous state and anhydrous amines are preferably employed, since water will react with the anhydride at longer reaction times (greater than 2 hours).

The pyromellitic acid anhydride monoamide (III) is then heated to form the pyromellitic imide anhydride (IV). The heating may take place in refluxing thionyl chloride and is complete in about 1–10 hours. No solvent is employed for heating in thionyl chloride. Alternatively the reaction may be heated in a high boiling solvent such as dimethylformamide, dimethylsulfoxide, dimethylacetamide, diphenyl ether and the like at from about 100° C. to the reflux temperature of the reaction mixture. The reaction is complete in about ½ to 1 hour. The reaction products (IV) are isolated following procedures known to those skilled in this art.

The pyromellitic imide anhydride (IV) is then treated with an amine (represented by $R_2NH_2$) in order to form the pyromellitic acid amide imide (V). The reaction is carried out very much in the manner of the first amine reaction (II to IV), however, since there is only a single anhydride function to be reacted, it is possible to use more than a single mole of the amine (from 1 to 2 molar equivalents are preferred) and to increase the reaction times, the reaction is generally complete in about 10 minutes to 4 hours at from 0° C. to room temperature.

Compound (V) is then heated either in thionyl chloride or dimethylformamide as described above in order to form the pyromellitic diimide compounds of this invention (I).

Alternatively the pyromellitic imide anhydride (IV) may be reacted without isolating the intermediate (V). The initial reaction with one mole of the amine may be carried out in a high boiling solvent such as dimethylformamide, but at the temperature conditions above described. Then, after the prescribed reaction times the reaction mixture may be slowly brought (over a period of from 1 to 4 hours) to the reaction conditions of the second step. The product (I) will be isolated in the usual manner.

An alternative procedure outlined in the above reaction sequence reacts compound (III) with a second mole of amine in order to form the $R_1$, $R_2$ disubstituted pyromellitic diamide (VI). The positioning of the bonds in structure (VI) indicates that a mixture of compounds is formed, viz the compound with $R_1$ on the upper carbonyl and the compound with $R_1$ on the lower carbonyl of the left side of the molecule. The mixture is not isolated, since both compounds of the mixture will form the same compound after the cyclization. The reaction is carried out using the same conditions used to form compound (V) from compound (IV).

Compound (VI) is then cyclized to the compounds of this invention (I) following the same procedure used to prepare compound (I) from compound (V), that is heating in thionyl chloride or dimethylformamido. The products are isolated using known techniques.

An alternate procedure, useful when one of $R_1$ or $R_2$ is hydrogen is outlined in the following reaction scheme:

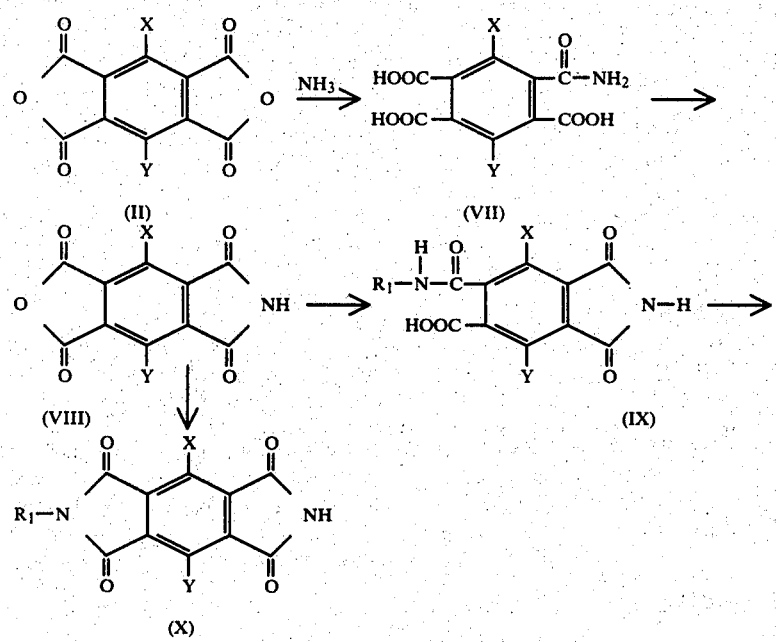

In the foregoing reaction scheme pyromellitic dianhydride (II) is treated with ammonia to prepare the 2,4,5-tricarboxybenzene-1-carbamate (VII). The reaction is generally carried out in a non-polar solvent in which the starting materials is soluble such as tetrahydrofuran, acetone, and the like and is complete in from 5 minutes to 2 hours at from 0° C. to room temperature. Room temperature is preferred.

Compound VII is then heated with thionyl chloride at about room temperature to the reflux temperature of the reaction mixture for from ½ to 6 hours to prepare the pyromellitic imide anhydride (VIII). Generally the reaction is carried out without any solvent using an excess of thionyl chloride, however, if desired, a nonpolar solvent, such a benzene or toluene may be employed. Alternatively the heating may be carried out in a high boiling solvent as described above to form compound (VIII).

Compound (VIII) is then treated with an $R_1$ substituted amine to react with the anhydride portion of compound (VIII) and prepare the $R_1$ carbamoyl compound (IX). The reaction is generally carried out in a solvent as described above and is complete in about 5 minutes to 2 hours at from about 10° to 50° C. Room temperature is preferred.

The carbamoyl compound (IX) is heated in a high boiling solvent as described above to prepare the $R_1$ monosubstituted pyromellitic diimide (X). The products are isolated using techniques known to those skilled in this art. Alternatively, the pyromellitic imide anhydride VIII may be reacted without isolating the intermediate IX as described for the reaction of IV to I.

Many of the compounds of this invention are conveniently prepared by reacting a substituent on the pyromellitic diimide moiety to prepare a different substituent. Such compounds are often also prepared by the above procedure, however, occasionally it is more convenient to delay the subsequent reaction until after the pyromellitic diimide compound is formed, in order to minimize side reactions, to facilitate the work-up procedures, and the like.

An example of such would be the reactions carried out on the N,N' hydroxyalkyl or aminoalkyl pyromellitic diimides. For the reactions preparing derivatives thereof, such as acyl derivatives, it is more convenient to acylate the N,N'-hydroxyalkyl or aminoalkyl compound than to use the acylated amino compound as starting material. While it is possible to carry out the reaction either way, the later acylation avoids the possibility that the acyl group will be removed by hydrolysis during the course of the reaction.

Such an acylation of the hydroxyalkyl, or aminoalkyl substituted pyromellitic diimide is carried out using standard acylation reagents such as the anhydride or halide of the acyl moiety. With lower molecular weight reagents such as acetic and propionic anhydride, the reagent is used as a solvent. For higher molecular weight reagents, where excess reagent would be more difficult to remove, an equivalent amount or a slight excess is employed and a basic inert solvent such as pyridine is employed. The reaction is carried out at from room temperature to the reflux temperature of the reaction mixture, preferably at from 75°–100° C., for from 5 minutes to 5 hours. The product is isolated using techniques known to those skilled in this art.

The compounds of the instant invention wherein the R-group contains a sulfur (thio) linkage are conveniently oxidized to the sulfinyl or sulfonyl linkages. This is carried out using mild oxidizing agents, such as m-chloroperbenzoic acid. A single molar equivalent is employed for the preparation of the sulfinyl group and two equivalents are used to prepare the sulfonyl group. The reaction is carried out in an inert solvent such as a halogenated hydrocarbon, (methylene chloride, chloroform, carbon tetrachloride, and the like) or a loweralkanol or mixtures thereof. The reaction is complete in from 10 minutes to 10 hours. To prepare the sulfinyl compound the temperature is generally maintained at room temperature. To prepare the sulfone, temperatures up to 100° C. or the reflux temperature are employed. The products are isolated using techniques used by those skilled in the art.

The compound where R is hydroxy methyl is generally prepared by reacting pyromellitic diimide (R=H) with formaldehyde in the presence of a base such as an alkali metal hydroxide, preferably sodium hydroxide. The reaction is carried out preferably in an aqueous solvent at from room temperature to 100° C. for from 1 to 10 hours. The products are isolated using known techniques.

In the course of investigating the efficiency of feed use, the mechanism by which ruminants digest and degrade the components of their feed to form molecules which can be metabolically utilized has been intensively studied. The mechanism of carbohydrate utilization is now well known. Microorganisms in the rumen of the animal ferment the carbohydrate to produce monosaccharides and then degrade the monosaccharides to pyruvate compounds.

Pyruvate is then metabolized by microbiological processes to either acetate or propionate compounds, which may be either acids or other forms of the radicals. Two acetate radicals may be combined thereafter, still in the rumen, to form butyrates.

The animal can utilize butyrate, propionate, and acetate with differing degrees of efficiency. Utilization of these compounds which are collectively known as volatile fatty acid (VFA) occurs after absorption from the gut of the animal. Butyrate is utilized most efficiently, and acetate the least efficiently. However, the relative efficiency of use to butyrate is negated by the inefficiency of the manufacture of butyrate, which must be made from acetate in the rumen.

One of the major inefficiencies in the rumen is in the manufacture of acetate. Since it is made by the degradation of a pyruvate molecule, each molecule of acetate which is produced is accompanied by a molecule of methane. Most of the methane produced is lost through eructation. Since butyrate is made from two molecules of acetate, each molecule of the relatively efficiently used butyrate involves the loss to the animal of two molecules of methane, with all of the associated energy.

Thus, the efficiency of carbohydrate utilization (carbohydrates being the major nutritive portion of ruminant animals' feed) can be increased by treatments which encourage the animal to produce propionate rather than acetate from the carbohydrates. Further, the efficiency of feed use can be effectively monitored by observing the production and concentration of propionate compounds in the rumen. If the animal is making more propionates, it will be found to be using its feed more efficiently. This efficiency is manifested by greater weight gains per feed intake, a reduction in energy losses by methane release, and economic advantages to the animal grower when the animal is sold for consumption.

The method of improving the feed utilization of ruminants of this invention comprises orally administering to a ruminant an effective amount of one or more of the above-described novel compounds. Of course, the most economically important ruminant animals (those with multiple stomachs, one of which functions as a rumen) are cattle, sheep and goats. The compounds of this invention are administered to ruminants orally at rates of from about 0.1 mg/kg/day to about 10 mg/kg/day. While that range is functional, the preferred range of rates is from about 0.5 to 5 mg/kg/day.

It has been found that the compounds of this invention increase the efficiency of feed utilization in ruminant animals. The easiest way to administer the compounds is by mixing them in the animal's feed. However, the compounds of this invention can be usefully administered in other ways. For example, they can be incorporated into tablets, drenches, boluses, or capsules, and dosed to the animals. Formulation of the compounds in such dosage forms can be accomplished by means and methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the desired compound. If desired, the compound can be diluted with an inert powdered diluent, such as a sugar, starch or purified crystalline cellulose, in order to increase its volume for convenience in filling capsules.

Tablets of the compounds useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

This method of increasing the efficiency of feed utilization can also be practiced by the administration of the instant compound as a slow-pay-out bolus. Such boluses are made as tablets are made, except that a means to delay the dissolution of the compound is provided. Boluses are made to release for lengthy periods. The slow dissolution is assisted by choosing a highly water-insoluble form of the compound. A substance such as iron filings is added to raise the density of the bolus and keep it static on the bottom of the rumen.

Dissolution of the compound is delayed by use of a matrix of insoluble materials in which the drug is embedded. For example, substances such as vegetable waxes, purified mineral waxes, and water insoluble polymeric materials are useful.

Drenches of the instant compounds are prepared most easily by choosing a water soluble or water dispersable form of the compound. If an insoluble form is desired for some reason, a suspension may be made. Alternatively, a drench may be formulated as a solution in a physiologically acceptable solvent such as a polyethylene glycol.

Suspension of insoluble forms of the compounds can be prepared in non-solvents such as vegetable oils such as peanut, corn, or sesame oil; in a glycol such as propylene glycol or a polyethylene glycol; or in water, depending on the form of the compound chosen.

Suitable physiologically acceptable adjuvants are necessary in order to keep the compound suspended. The adjuvants can be chosen from among the thickeners, such as carboxymethylcellulose, polyvinylpyrrolidone, gelatin, and the alginates. Many classes of surfactants also will serve to suspend the compounds. For example, lecithin, alkylphenol polyethylene oxide adducts, naphthalene sulfonates, alkylbenzenesulfonates and the polyoxyethylene sorbitan esters are useful for making suspension in liquid nonsolvents.

In addition, many substances which effect the hydrophilicity, density, and surface tension of the liquid can assist in making suspensions in individual cases. For example, silicone antifoams, glycols, sorbitol, and sugars can be useful suspending agents.

The suspendable compound may be offered to the animal grower as a suspension, or as a dry mixture of the compound and adjuvants to be diluted before use.

These compounds may also be administered in the drinking water of the ruminants. Incorporation into drinking water is performed by adding a water soluble or water suspendable form of desired compound to the water in the proper amount. Formulation of the compound for addition to drinking water follows the same principles as formulation of drenches.

The most practical way to treat animals with the compounds of this invention usable in this novel method is by the formulation of the compound into the feed supply. Any type of feed may be medicated with the instant compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 1 to about 400 g. of drug per pound (454 g.) of premix. The wide range results from the wide range of concentration of drug which may be desired in the final feed. Premixes may be either liquid or solid.

The formulation of ruminant feeds containing the proper amounts of the instant compounds for useful treatment is mainly a matter of arithmetic. It is necessary only to calculate the amount of compound which it is desired to administer to each animal, to take into account the amount of feed per day which the animal eats, and the concentration of compound in the premix to be used, and calculate the proper concentration of the compound in the feed.

All of the methods of formulation, mixing, and pelleting feeds which are normally used in the ruminant feed art are entirely appropriate for manufacturing feeds containing the compounds usable in this method.

It is not intended that the scope of this invention be limited to any particular formulations or methods of administration. The invention is a method of increasing the efficiency of feed utilization by ruminant animals by the oral administration of certain compounds regardless of the method of administration of the compounds.

It is usual to treat economic animals, including ruminants, with a variety of growth promoters, disease preventives, and disease treatments throughout their lives. Such drugs are often used in combination. The novel method may be practiced in combination with other treatments.

EXAMPLE 1

2,4,5-Tricarboxybenzamide 17.44 G. of pyromellitic dianhydride is dissolved in 200 ml. of tetrahydrofuran and stirred at room temperature while 10 ml. of water is added. The reaction mixture is stirred at room temperature for 12 minutes and cooled in ice. 60 G. of anhydrous magnesium sulfate is added and the reaction mixture stirred at 0° C. for 15 minutes. The ice bath is removed and the reaction mixture is allowed to warm to room temperature. Stirring is continued at room temperature for 35 minutes and the reaction mixture is filtered and the insoluble material washed twice with 100 ml. portions of tetrahydrofuran. The filtrate is cooled and anhydrous ammonia is bubbled in rapidly forming a precipitate. The reaction mixture becomes thick and 200 ml. of acetone is added to increase the efficiency of the stirring. The solution is saturated with ammonia at 0° C. and stirred an additional 20 minutes. The insoluble material is filtered and washed with acetone and dried affording 24.9 g. of a white solid which is identified by nuclear magnetic resonance as 2,4,5-tricarboxybenzamide.

EXAMPLE 2

Pyromellitic imide anhydride

90 G. of 2,4,5-tricarboxybenzeneamide is added to 900 ml. of thionylchloride with stirring at room temperature. The reaction mixture is heated at reflux for 2 hours. Upon cooling, 900 ml. of hexane is added and the mixture stirred for 30 minutes. The insoluble material is filtered, washed with hexane and dried at 80° C. under vacuum affording 89.3 g. of a light yellow solid identified by infrared spectroscopy as pyromellitic imide anhydride.

EXAMPLE 3

1 N-Methylcarbamoyl-2-carboxybenzene 4,5-dicarboxylic acid imide 2.17 G. of pyromellitic imide anhydride is dissolved in 75 ml. of acetone and stirred at 0° C. while 1.94 g. of a 40% aqueous solution of methylamine dissolved in 20 ml. of acetone is added dropwise over 20 minutes. When the addition is complete, the reaction is concentrated to dryness at room temperature under vacuum. The residue is dissolved in 13 ml. of water and centrifuged, separating out the solid materials. The insoluble materials are washed with 3.0 ml. of water and the combined aqueous phases are acidified to pH 1 with 2.5 N-hydrochloric acid and stirred at 0° C. affording a precipitate. The mixture is filtered and the solid material washed with water, ethanol and twice with ether. The solid is dried in air affording 1.482 g. of a white solid identified by nuclear magnetic resonance as 1 N-methylcarbamoyl-2-carboxybenzene 4,5-dicarboxylic acid imide.

EXAMPLE 4

1 N-Ethylcarbamoyl 2-carboxybenzene 4,5-dicarboxylic acid imide 1.05 G. of pyromellitic imide anhydride is dissolved in 35 ml. of acetone and cooled to 0° C., 544 mg. of ethylamine dissolved in 10 ml. of acetone is added dropwise with stirring at 0° C. over a period of 15 minutes. The reaction mixture stirred at 0° C. for 20 minutes and concentrated to dryness in vacuo. The residue is dissolved in 9 ml. of water and centrifuged to remove the insoluble material. The supernatant liquid is acidified with 2.5 N hydrochloric acid to pH 1 affording white crystals. The mixture is stirred at room temperature for 20 minutes and filtered. The solids are washed twice with water, once with ethanol and twice with ether and dried affording 854 mg. of a white solid identified by nuclear magnetic resonance as 1 N-ethylcarbamoyl 2-carboxybenzene 4,5-dicarboxylic acid imide.

EXAMPLE 5

1 N-(n-Propyl) carbamoyl 2-carboxybenzene 4,5-dicarboxylic acid imide

Following the procedure of Example 4 using 1.09 g. of pyromellitic imide anhydride 40 ml. of acetone and 739 mg. of n-propylamine there is produced 1.125 g. of a white solid identified by nuclear magnetic resonance as 1 N(n-propyl) carbamoyl 2-carboxybenzene 4,5-dicarboxylic acid imide.

EXAMPLE 6

1 N-(2-Hydroxyethyl)carbamoyl 2-carboxybenzene, 4,5-dicarboxylic acid imide

Following the procedure of Example 3 using 15.0 g. of pyromellitic imide anhydride in 520 ml. of acetone and 10.4 ml. of 2-aminoethanol dissolved in 140 ml. of acetone. There is produced 10.70 g. of an off-white solid identified by nuclear magnetic resonance as 1 N-(2-hydroxyethyl)carbamoyl 2-carboxybenzene 4,5-dicarboxylic acid imide.

EXAMPLE 7

1 N-Allylcarbamoyl 2-carboxybenzene 4,5-dicarboxylic acid imide 1.0 G of pyromellitic imide anhydride is suspended in 3 ml. dimethylformamide and cooled in an ice bath dropwise 0.7 g. of allylamine and 2 ml. of dimethylformamide is added. The resulting solution is stirred at room temperature for 45 minutes. The reaction mixture is diluted with 3 to 5 volumes of ether, filtered and the solid material washed 3 times with ether. The solid material is dissolved in a minimum amount (about 5 ml.) of water and treated with 2.5 N hydrochloric acid to pH 1. The aqueous solution is stirred at room temperature for 1 hour. The precipitate is filtered, washed with water, 5 times with ether and dried in vacuo at 90° C. affording 549 mg. of a solid material with a m.p. of 230°–232° C. and identified by nuclear magnetic resonance as 1 N-allylcarbamoyl 2-carboxybenzene 4,5-dicarboxylic acid imide.

EXAMPLE 8

N-(n-Propyl) pyromellitic diimide

800 Mg. of 1 N(n-propyl) carbamoyl 2-carboxybenzene 4,5-dicarboxylic acid imide is suspended in 3 ml. of dry dimethylformamide and immersed in an oil bath at 100° C. whereupon the mixture became homogeneous. The reaction mixture is further heated to 150° C. for 45 minutes. Upon cooling to room temperature, the mixture is stirred overnight and filtered, the solid material is washed once with dimethylformamide, once with alcohol and twice with ether. Upon drying in air, there is afforded 223 mg. of white crystals, m.p. 260°–261° C., identified by nuclear magnetic resonance as N-(n-propyl) pyromellitic diimide.

EXAMPLE 9

N-(2-Hydroxyethyl) pyromellitic diimide

Following the procedure of Example 8 using 10.65 g. of 1 N-(2-hydroxyethyl) carbamoyl 2-carboxybenzene 4,5-dicarboxylic acid imide in 32 ml. of dimethylformamide there is prepared 7.325 g. of an off-white solid identified by nuclear magnetic resonance as N-(2-hydroxyethyl) pyromellitic diimide.

EXAMPLE 10

1 -N-Methylcarbamoyl-2-carboxybenzene 4,5-dicarboxylic acid anhydride

60 G. of pyromellitic dianhydride is suspended in 800 ml. of acetone and treated with 18.12 g. of 40% aqueous methylamine in 100 ml. of acetone at 10° C. The reaction mixture is stirred for 20 minutes and filtered. The acetone filtrate is evaporated to dryness and the residue triturated with 1000 ml. of refluxing ethylacetate. The mixture is filtered hot, and the insoluble material washed once with hot ethylacetate affording 40.6 g. of 1 N-methylcarbamoyl 2-carboxybenzene 4,5-dicarboxylic acid anhydride m.p. 266°–268° C. Nuclear magnetic resonance confirms the above structure.

EXAMPLE 11

N-Methyl benzene 4,5-dicarboxylic acid imide 1,2-dicarboxillic acid anhydride 39 G. of 1 N-methylcarbamoyl 2-carboxybenzene 4,5-dicarboxylic acid anhydride is added to 300 ml. of thionyl chloride and refluxed for 4 hours. The reaction mixture is cooled and diluted with 300 ml. of benzene. The mixture is filtered and the solid material washed once with benzene and 3 times with petroleum ether. The solid is dried at 45° C. in vacuo affording 32.56 g. of N-methyl benzene 4,5-dicarboxylic acid imide 1,2-dicarboxylic acid anhydride m.p. 265°–267° C.

EXAMPLE 12

1-Carbamoyl 2-carboxybenzene N-methyl 4,5-dicarboxylic acid amide

15 G. of N-methyl benzene-4,5-dicarboxylic acid amide 1,2-dicarboxylic acid anhydride is suspended in 750 ml. of acetone and treated with ammonia gas at 10° C. for about 10 minutes. The reaction mixture is allowed to warm to room temperature and evaporated to dryness in vacuo. The residue is dissolved in 100 ml. of water and filtered. The water layer is treated with 2.5 N hydrochloric acid to a pH of 1.5 and the resulting precipitate filtered, washed once with water, twice with ethanol, twice with ether and dried at 50° C. in vacuo affording 13.9 g. of 1-carbamoyl 2-carboxybenzene N-methyl 4,5-dicarboxylic acid amide.

EXAMPLE 13

N-Methyl pyromellitic diimide 13.9 G. of 1-carbamoyl 2-carboxybenzene N-methyl 4,5-dicarboxylic acid imide is dissolved in 55 ml. of dimethylformamide and heated at reflux for 45 minutes. The mixture is cooled, diluted with an equal volume of ethanol, filtered, washed once with ethanol and 3 times with ether. The solid material is dried at 100° C. in vacuo affording 8.64 g. of N-methyl pyromellitic diimide m.p. in excess of 320° C.

EXAMPLE 14

1 N-Ethylcarbamoyl 2-carboxybenzene N-methyl 4,5-dicarboxylic acid imide

15 G. of N-methyl benzene 4,5-dicarboxylic acid imide 1,2-dicarboxylic acid anhydride is dissolved at 750 ml. of acetone and combined with 7.3 g. of ethylamine in 50 ml. of acetone in 1 portion at 10° C. The reaction mixture is stirred for 30 minutes, filtered, the solid material washed once with acetone, 3 times with ether and dried at 40° C. in vacuo affording 19.5 g. of 1 N-ethylcarbamoyl 2-carboxybenzene N-methyl 4,5-dicarboxylic acid imide the structure of which is confirmed by nuclear magnetic resonance.

EXAMPLE 15

N-Methyl N'-Ethyl pyromellitic diimide 19.5 G. of 1 N-ethyl carbamoyl 2-carboxybenzene N-methyl 4,5-dicarboxylic acid imide is dissolved in 110 ml. of dimethylformamide and heated at reflux for 45 minutes. The reaction mixture is cooled slightly and diluted with 110 ml. of ethanol resulting in a colorless precipitate. The suspension is cooled, filtered and the solid material washed once with ethanol, 3 times with ether and dried at 100° C. in vacuo affording 9.8 g. of N-methyl N'-ethyl pyromellitic diimide m.p. 287°-288.5° C.

EXAMPLE 16

1 N-Ethyl carbamoyl 2-carboxy 4,5-dicarboxylic acid anhydride

30 G. of pyromellitic dianhydride is suspended in 400 ml. of acetone and treated dropwise over 45 minutes with 7.5 g. of ethylamine in 70 ml. of acetone at room temperature. The reaction mixture is stirred and additional 45 minutes and filtered. The solid material is washed with acetone and the combined acetone, filtrate and washings are evaporated to dryness in vacuo affording 29.6 g. of a solid material which is combined with 1500 ml. of ethylacetate and heated to reflux. The ethylacetate suspension is filtered hot and the insoluble material washed once with ethylacetate and dried at 70° C. in vacuo affording 8.0 g. of 1 N-ethyl carbamoyl 2-carboxy 4,5-dicarboxylic acid anhydride m.p. 170°-172° C. The structure of the material is confirmed by nuclear magnetic resonance.

EXAMPLE 17

N-Ethyl benzene 1,2-carboxylic acid imide 4,5-dicarboxylic acid anhydride 1.0 G. of 1 N-ethyl carbamoyl 2-carboxybenzene 4,5-dicarboxylic acid anhydride is dissolved in 15 ml. of benzene and 2.0 ml. of thionyl chloride and heated at reflux for 1 hour. The reaction mixture is cooled and evaporated to dryness in vacuo. The solid material is washed twice with benzene affording N-ethyl benzene 1,2-carboxylic acid imide 4,5-dicarboxylic acid anhydride the structure of which is confirmed by nuclear magnetic resonance.

EXAMPLE 18

1-Carbamoyl 2-carboxybenzene N-ethyl 4,5-dicarboxylic acid imide

The total crude material from the previous example is suspended in 10 ml. of acetone and treated with ammonia gas for 5 minutes. The reaction mixture becomes very thick and an additional 10 ml. of acetone is added. The reaction mixture is filtered and the solid material washed with acetone. The solid material is dissolved in 20 ml. of water and treated with 2.5 N hydrochloric acid to pH 5 whereupon a precipitate results which is filtered, washed twice with water, once with ethanol and twice with ether affording 600 mg. of 1-carbamoyl 2-carboxybenzene N-ethyl 4,5-dicarboxylic acid imide m.p. 325°-327° C. with decomposition. The structure is confirmed with nuclear magnetic resonance.

EXAMPLE 19

N-Ethyl pyromellitic diimide

550 Mg. of 1-carbamoyl 2-carboxybenzene N-ethyl 4,5-dicarboxylic acid imide is dissolved in 3.0 ml. of dimethylformamide and heated at reflux for 45 minutes. Upon cooling, a precipitate results and the mixture is diluted with 3 ml. of ethanol, filtered and the solid material washed once with ethanol and once with ether affording 250 mg. of N-ethyl pyromellitic diimide m.p. 331°-332° C. The structure is confirmed by nuclear magnetic resonance.

EXAMPLE 20 n N-Methyl carbamoyl 2-carboxybenzene N-ethyl 4,5-dicarboxylic acid imide 1.0 G. of N-ethylbenzene 1,2-dicarboxylic acid imide 4,5-dicarboxylic acid anhydride is dissolved in 10 ml. of acetone and treated with gaseous methylamine for 5 minutes at room temperature. The reaction mixture is stirred at room temperature for 20 minutes and evaporated to dryness in vacuo. The residue is suspended in 30 ml. of water, filtered and treated with 2.5 N hydrochloric acid affording a precipitate. The precipitate is filtered, washed twice with water and dried at 90° C. in vacuo affording 1 N-methyl carbamoyl 2-carboxybenzene N-ethyl 4,5-dicarboxylic acid imide m.p. 288°-289° C. The structure is confirmed by nuclear magnetic resonance.

EXAMPLE 21

N-Ethyl N'-methyl pyromellitic diimide 0.55 G. of 1 N-methyl carbamoyl 2-carboxybenzene N-ethyl 4,5-dicarboxylic acid imide is dissolved in 2 ml. of dimethylformamide and heated at reflux for 45 minutes. The reaction mixture is cooled, treated with an equal volume of ethanol affording a precipitate. The mixture is filtered and the solid material washed once with ethanol and once with ether affording 400 mg. of N-ethyl N'-methyl pyromellitic diimide m.p. 285°-287° C. The structure is confirmed by nuclear magnetic resonance.

EXAMPLE 22

N-Methyl pyromellitic diimide 9.3 Ml. (0.21 mole) of liquid methylamine is delivered as a gas into a stirred suspension of pyromellitic imide anhydride, 43.4 g. (0.20 mole), in 600 ml. of dimethylformamide. The mixture is stirred at room temperature for 1 hour, at 50° C. for 30 minutes, at 75° C. for 30 minutes and at 150° C. for 1 hour, and then about 400 ml. of dimethylformamide is removed by distillation. The concentrate is cooled in ice and diluted with 3 volumes of ethanol. Cooling is continued until crystallization is complete. The crystals are collected, rinsed with cold ethanol, cold ethyl ether and dried in vacuo at 70° C. furnishing 35.2 g. of N-methyl pyromellitic diimide m.p. 300° C.

EXAMPLE 23

N-Allyl pyromellitic diimide 13.0 G. (60 mmole) of pyromellitic imide anhydride is added at room temperature (23° C.) with stirring under nitrogen to a solution of allylamine, 4.73 ml. (63 mmole) in 60 ml. of dimethylformamide. The mixture is stirred at room temperature for 30 minutes, at 50° C. for 30 minutes, at 100° C. for 30 minutes, and at 150° C. for 1 hours, and then cooled in ice. Three volumes of ethanol are added and cooling is continued until crystallization is complete. The crystals are collected, rinsed with cold ethanol and cold ethyl ether and then dried in vacuo at 70° C. furnishing 8.3 g. of N-allyl pyromellitic diimide m.p. 248.5°–249.5° C.

TABLE I

N-Monosubstituted Pyromellitic Diimides with Hydrocarbon Side Chains as Prepared in Examples 4, 13 or 23

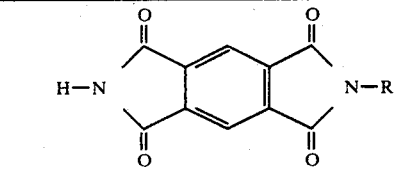

| Hydrocarbon Amine Reactant | Pyromellitic Diimide Product (R) | m.p. °C. |
|---|---|---|
| Methylamine | N-methyl | >300 |
| Ethylamine | N-ethyl | 331–332 |
| n-propylamine | N-(n-propyl) | 260–261 |
| n-butylamine | N-(n-butyl) | 257–258 |
| n-pentylamine | N-(n-pentyl) | 255–256 |
| n-hexylamine | N-(n-hexyl) | 243.5–245 |
| i-propylamine | N-(i-propyl) | 274–276 |
| Allylamine | N-allyl | 248.5–249.5 |
| Propargylamine | N-(2-propyn-1-yl) | 288–289 |
| Cyclopropylamine | N-cyclopropyl | >300 |
| Cyclobutylamine | N-cyclobutyl | |
| Cyclopentylamine | N-cyclopentyl | 267–268 |

TABLE I-continued

N-Monosubstituted Pyromellitic Diimides with Hydrocarbon Side Chains as Prepared in Examples 4, 13 or 23

| Hydrocarbon Amine Reactant | Pyromellitic Diimide Product (R) | m.p. °C. |
|---|---|---|
| Cyclohexylamine | N-cyclohexyl | 305.5–307 |
| Benzylamine | N-benzyl | 286–287 |
| Phenethylamine | N-phenethyl | 283–285 |

EXAMPLE 24

N-(2-Hydroxyethyl) pyromellitic diimide

300 G. (1.38 mole) pyromellitic imide anhydride is added with stirring at room temperature (23° C.) to a solution of 95% ethanolamine, 83.4 ml. (1.38 mole) in 1.5 l. of dimethylformamide. The mixture is stirred at room temperature for 30 minutes, at 50° C. for 30 minutes, at 75° C. for 30 minutes, at 150° C. for 45 minutes, and then cooled in ice. 3 L. of ethanol are added and cooling is continued until crystallization is complete. The crystals are collected, rinsed with cold ethanol, cold ethyl ether and then dried in vacuo at 70° C. furnishing 292 g. of N-(2-hydroxyethyl) pyromellitic diimide m.p. 274°–5° C. Recrystallization from dimethylformamide gives a purified product m.p. 279°–280° C.

TABLE II

N-Monosubstituted Pyromellitic Diimides with Hydroxy in the Side Chain as Prepared in Examples 4, 13 or 24

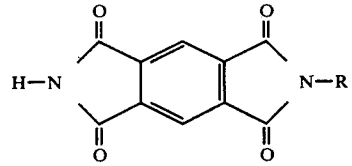

| Amine Reactant | Pyromellitic Diimide Product (R) | m.p. °C. |
|---|---|---|
| Ethanolamine | N-(2-Hydroxyethyl) | 279–280 |
| 3-Amino-1-propanol | N-(3-Hydroxyprop-1-yl) | 258–260 |
| 4-Amino-1-butanol | N-(4-Hydroxybut-1-yl) | 232–233 |
| 5-Amino-1-pentanol | N-(5-Hydroxypent-1-yl) | 123.5–124 |
| 6-Amino-1-hexanol | N-(6-Hydroxyhex-1-yl) | 218–219.5 |
| 1-Amino-2-propanol | N-(2-Hydroxyprop-1-yl) | 245–246.5 |
| 2-Amino-1-butanol | N-(1-Hydroxybut-2-yl) | 204–205 |
| 2-Amino-2-methyl-1-propanol | N-(1-Hydroxy-2-methylprop-2-yl) | 245–246.5 |
| 3-Amino-1,2-propanediol | N-(2,3-Dihydroxyprop-1-yl) | 259–261 |
| 2-Amino-1,3-propanediol | N-(2-methyl-1,3-dihydroxyprop-1-yl) | 263–264.5 |
| 2-Amino-1-phenylethanol | N-(1-Hydroxy-1-phenyleth-2-yl) | |
| 2-(4-Aminophenyl)ethanol | N-[4-(2-Hydroxyethyl)phen-1-yl] | |
| 2-[(2-Aminoethyl)-thio]ethanol | N-[2-(2-Hydroxyethyl)thioeth-1-yl] | 215–216 |
| 2-(2-Aminoethoxy)ethanol | N-[2-(2-Hydroxyethoxy)eth-1-yl] | 232.5–233.5 |
| N-(3-Aminopropyl)diethanolamine | N-{3-[di(2-hydroxyethyl)amino]prop-1-yl} | 140–143 |
| N-(2-Hydroxyethyl)ethylenediamine | N-[2-(2-Hydroxyethyl)aminoeth-1-yl] | |

EXAMPLE 25

N-(2-Mercaptoethyl)pyromellitic diimide

To an ice cooled mixture containing 13.0 g. (60 mmole) of pyromellitic imide anhydride and 6.82 g. (60 mmole) of 2-aminoethanethiol hydrochloride in 60 ml.

of dry dimethylformamide is added dropwise with stirring 8.36 ml. (60 mmole) of dry triethylamine. The mixture is stirred at room temperature (23° C.) for 30 minutes, at 50° C. for 30 minutes, at 75° C. for 30 minutes and at 100° C. for 45 minutes and then cooled in ice and diluted with 600 ml. of water. The insolubles are collected, rinsed with cold water, cold ethanol, and cold ethyl ether and then dried furnishing 13.0 g. of N-(2-mercaptoethyl) pyromellitic diimide, m.p. 300° C.

EXAMPLE 28

N-(2-Aminoethyl)pyromellitic diimide

To a stirred solution of liquid ammonia, 22 ml. (1.0 mole), in 200 ml. of dimethylformamide is added portionwise 3.2 g. (10 mmole) of N-(2-bromoethyl)pyromellitic diimide. The mixture is stirred at room temperature (23° C.) for 48 hours. Excess ammonia is removed by concentration under reduced pressure without heating. Several volumes of dilute aqueous sodium carbonate are added to the concentrate with ice bath cooling. The insolubles are collected, rinsed with water, cold methanol, and ethyl ether furnishing N-(2-aminoethyl)-pyromellitic diimide.

TABLE III

N-Monosubstituted Pyromellitic Diimide with Substituted Alkyl Side Chains as Prepared in Examples 4, 13, 24 or 25

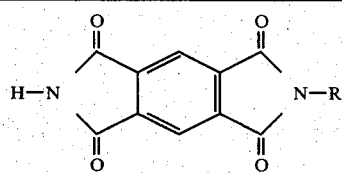

| Amine Reactant | Pyromellitic Diimide Product (R) | m.p. °C. |
|---|---|---|
| 2-Methoxyethylamine | N-(2-Methoxyethyl) | 250–251 |
| 2-Aminoethanethiolhydrochloride | N-(2-Mercaptoethyl) | >300 |
| 2-Methylmercaptoethylamine | N-(2-Methylthioethyl) | 253–254 |
| Glycine | N-(Carboxymethyl) | >300 |
| β-Alanine | N-(2-Carboxyethyl) | |
| Glycinamide hydrochloride | N-(Carbamylmethyl) | >300 |
| Glycine ethyl ester hydrochloride | N-(Carbethoxymethyl) | >300 |
| 2-Dimethylaminoethylamine | N-(2-Dimethylaminoethyl) | 255–257 |
| 3-Dimethylaminopropylamine | N-(3-Dimethylaminopropyl) | 211.5–213 |
| N-Acetylenediamine | N-(N-Acetylaminoethyl) | |
| 2-Chloroethylamine hydrochloride | N-(2-Chloroethyl) | |
| 2-Bromoethylamine hydrobromide | N-(2-Bromoethyl) | |
| 2-Nitroethylamine | N-(2-Nitroethyl) | |

EXAMPLE 26

N-(2-Methylsulfinylethyl) pyromellitic diimide

To a solution of N-(2-methylmercaptoethyl) pyromellitic diimide, 8.0 g. (27 mmole) in 700 ml. of methanol-methylenechloride (1:9) is added dropwise a solution of 85% m-chloroperoxybenzoic acid 5.6 g. (27 mmole) in 250 ml. of methylene chloride. Stirring is continued for 60 minutes longer at room temperature (23° C.) and then the solution is cooled in ice. The insolubles are collected, rinsed with cold methylene chloride and dried furnishing 8.0 g. of N-(2-methylsulfinylethyl) pyromellitic diimide, m.p. 280°–281° C.

EXAMPLE 27

N-(2-Methylsulfonylethyl) pyromellitic diimide

To 8.2 g. (28 mmole) of N-(methylmercaptoethyl) pyromellitic diimide suspended in 960 ml. of glacial acetic acid is added with stirring at room temperature (23° C.) 14.5 g. (71 mmole) of 85% m-chloroperoxybenzoic acid. The mixture is heated at 100° C. for 4 hours and then cooled in ice. The insolubles are collected, rinsed with cold methylenechloride furnishing 7.8 g. of N-(methylsulfonylethyl) pyromellitic diimide, m.p. 291°–292° C.

EXAMPLE 29

N-(2-Methylaminoethyl)pyromellitic diimide

Following the procedure of Example 28 using 22 ml. (0.5 mole) of liquid methylamine in place of the ammonia and stirring the mixture for 16 hours provides N-(2-methylaminoethyl)pyromellitic diimide.

EXAMPLE 30

N-Acetoxy-N'-(2-hydroxyethyl)pyromellitic diimide

To a solution of acetic anhydride, 0.83 ml. (8.8 mmole) in 50 ml. of dry pyridine is added with stirring 2.08 g. (8.0 mmole) of N-(2-hydroxyethyl)pyromellitic diimide at room temperature. Stirring is continued for 90 minutes. The solution is cooled in ice and diluted with ethyl ether till turbid. The resulting insolubles are removed by filtration. The filtrate is diluted with ethyl ether and cooled. The insolubles are collected, rinsed with ether and dried furnishing 1.5 g. of N-acetoxy-N'-(2-hydroxyethyl)pyromellitic diimide, m.p. 193.5°–195.0° C.

TABLE IV

Unsymmetrical N,N'-Disubstituted Pyromellitic Diimides with N-Alkanoyl-N'-Hydroxyalkyl and Related Side Chains as prepared in Example 30

[Structure: R-C(=O)-N< pyromellitic diimide >N-R']

| Pyromellitic Diimide Reactant | Pyromellitic Diimide Product (R,R') | m.p. °C. |
|---|---|---|
| N-(2-Hydroxyethyl) | N-Acety-N'-(2-hydroxyethyl) | 193.5–195 |
| N-(3-Hydroxyprop-1-yl) | N-Acetyl-N'-(3-hydroxyprop-1-yl) | |
| N-(4-Hydroxybut-1-yl) | N-Acetyl-N'-(4-hydroxybut-1-yl) | |
| N-(5-Hydroxypent-1-yl) | N-Acetyl-N'-(5-hydroxypent-1-yl) | |
| N-(6-Hydroxyhex-1-yl) | N-Acetyl-N'-(6-hydroxyhex-1-yl) | |
| N-(1-Hydroxbut-2-yl) | N-Acetyl-N'-(1-hydroxybut-2-yl) | |
| N-[2-(2-Hydroxyethyl)thioeth-1-yl] | N-Acetyl-N'-[2-(2-hydroxyethyl)thioethy-1-yl] | |
| N-[2-(2-Hydroxyethoxy)eth-1-yl] | N-Acetyl-N'-[2-(2-hydroxyethoxy)eth-1-yl] | |

EXAMPLE 31

N-Acetyl-N'-(2-acetoxyethyl)pyromellitic diimide

To a solution of acetic anhydride, 18.8 ml. (200 mmole) in 156 ml. of dry pyridine is added with stirring at room temperature (23° C.) 10.4 g. (40 mmole) of powdered N-(2-hydroxyethyl)pyromellitic diimide. The mixture is heated at 100° C. for 2 hours and then cooled in ice and diluted with ethyl ether. The insolubles are collected, rinsed with cold ethyl ether and dried furnishing 11.0 g. of N-acetyl-N'-(2-acetoxyethyl)pyromellitic diimide, m.p. 176°–8° C.

TABLE V

Unsymmetrical N,N'-Disubstituted Pyromellitic Diimides with N-Alkanoyl-N'-Alkanoyloxyalkyl and Related Side Chains as prepared in Example 31

[Structure: R-C(=O)-N< pyromellitic diimide >N-R']

| Pyromellitic Diimide Reactant | Pyromellitic Diimide Product (R,R') | m.p. °C. |
|---|---|---|
| N-(2-Hydroxyethyl) | N-Acetyl-N'-(2-acetoxyethyl) | 176–178 |
| N-(3-Hydroxyprop-1-yl) | N-Acetyl-N'-(3-acetoxyprop-1-yl) | |
| N-(4-Hydroxybut-1-yl) | N-Acetyl-N'-(4-acetoxybut-1-yl) | |
| N-(5-Hydroxypent-1-yl) | N-Acetyl-N'-(5-acetoxypent-1-yl) | |
| N-(6-Hydroxyhex-1-yl) | N-Acetyl-N'-(6-acetoxyhex-1-yl) | |
| N-(1-Hydroxybut-2-yl) | N-Acetyl-N'-(1-acetoxybut-2-yl) | |
| N-[2-(2-Hydroxyethyl)thioeth-1-yl] | N-Acetyl-N'-[2-(2-acetoxyethyl)thioeth-1-yl] | 134–135 |
| N-[2-(2-Hydroxyethoxy)eth-1-yl] | N-Acetyl-N'-[2-(2-acetoxyethoxy)eth-1-yl] | 152–153 |

EXAMPLE 32

N-(2-Acetoxyethyl)pyromellitic diimide

N-Acetyl-N'-(2-acetoxyethyl)pyromellitic diimide, 1.0 g., in 60 ml. of water dioxane (1:5) is stirred at reflux for 1 hour. The solution is cooled in ice, diluted with water and then concentrated under reduced pressure till crystals separate. The crystals are filtered, rinsed with cold water and air dried with suction furnishing 0.15 g. of N-(2-acetoxyethyl)pyromellitic diimide.

TABLE VI

N-Monosubstituted Pyromellitic Diimides with Alkanoyloxyalkyl and Related Side Chains as prepared in Example 32

[Structure: H-N< pyromellitic diimide >N-R]

| Pyromellitic Diimide Reactants | Pyromellitic Diimide Products (R) | m.p. °C. |
|---|---|---|
| N-Acetyl-N'-(2-acetoxyethyl) | N-(2-acetoxyethyl) | |
| N-Acetyl-N'-(3-acetoxyprop-1-yl) | N-(3-acetoxyprop-1-yl) | |
| N-Acetyl-N'-(4-acetoxybut-1-yl) | N-(4-acetoxybut-1-yl) | |
| N-Acetyl-N'-(5-acetoxypent-1-yl) | N-(5-acetoxypent-1-yl) | |
| N-Acetyl-N'-(6-acetoxyhex-1-yl) | N-(6-acetoxyhex-1-yl) | |
| N-Acetyl-N'-(1-acetoxybut-2-yl) | N-(1-acetoxybut-2-yl) | |
| N-Acetyl-N'-[2-(2-acetoxyethyl)thioeth-1-yl] | N-[2-(2-acetoxyethyl)thioeth-1-yl] | |
| N-Acetyl-N'-[2-(2-acetoxyethoxy)eth-1-yl] | N-[2-(2-acetoxyethoxy)eth-1-yl] | |

EXAMPLE 33

N-Acetyl pyromellitic diimide

Powdered pyromellitic diimide, 30.3 g. (0.14 mole), is added all at once to a vigorously stirred solution of acetic anhydride, 14.5 ml. (0.154 mole), in 1.25 l. of reagent pyridine at room temperature (21° C.). Stirring is continued for 2 hours. The mixture stands at room temperature overnight, 16 hours and then is cooled in ice. The insolubles are collected, rinsed with a small amount of cold pyridine, cold methanol, then thoroughly with ethyl ether and dried furnishing 26.6 g. of N-acetyl pyromellitic diimide, m.p. 268°–270° C. dec.

TABLE VII

N-Monosubstituted Pyromellitic Diimides with Alkanoyl and Benzoyl Side Chains as Prepared by Example 33

| Anhydride Reactant | Pyromellitic Diimide Product (R) | m.p. 0° C. |
|---|---|---|
| Acetic | N-acetyl | 268–270 |
| Propionic | N-propionyl | >300 |
| Butyric | N-butyryl | >300 |
| Valeric | N-valeryl | |
| Hexanoic | N-hexanoyl | >300 |
| Benzoic | N-benozyl | >300 |

EXAMPLE 34

N-(4-Hydroxyphenyl)pyromellitic diimide

Pyromellitic imide anhydride, 2.17 g. (10 mmole) is added with stirring at room temperature (23° C.) to a solution of 4-aminophenol 1.20 g. (10 mmole) in 10 ml. of dimethylformamide under nitrogen. The mixture is stirred for 30 minutes at room temperature, for 30 minutes at 50° C., for 30 minutes at 100° C. and for 1 hour at 150° C. and then cooled in ice and diluted with 3 volumes of ethanol. The crystals are collected, rinsed with cold ethanol and with ethyl ether furnishing 2.30 g. of N-(4-hydroxyphenyl)pyromellitic diimide, m.p. 300° C.

TABLE VIII

N-Monosubstituted Pyromellitic Diimides with Substituted Phenyl Side Chains as prepared by Example 34

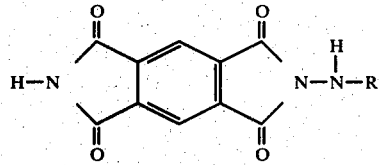

| Amine Reactant | Pyromellitic Diimide Product | m.p. °C. |
|---|---|---|
| 4-Aminophenol | N-(4-Hydroxyphenyl) | >300 |
| Sulfanilamide | N-(4-Sulfamylphenyl) | >300 |
| 4-Aminobenzoic Acid | N-(4-Carboxyphenyl) | >300 |
| 4-Nitroaniline | N-(4-Nitrophenyl) | >300 |
| 4-Methylmercaptoaniline hydrochloride | N-(4-Methylthiophenyl) | >300 |

EXAMPLE 35

N-(Dimethylamino)pyromellitic diimide

To a solution of unsym. dimethylhydrazine, 1.52 g. (20 mmole), in 20 ml. of dimethylformamide is added with stirring under nitrogen 4.34 g. (20 mmole) of pyromellitic imide anhydride. The mixture is stirred at room temperature for 30 minutes, at 50° C. for 30 minutes, at 75° C. for 30 minutes and at 150° C. for 45 minutes, and then cooled and diluted with water. The resulting crystals are collected, rinsed with cold water, cold ethanol, and cold ether and dried furnishing 1.60 g. of N-(dimethylamino)pyromellitic diimide, m.p. 293°–5° C.

TABLE IX

N-Monosubstituted Pyromellitic Diimides with Substituted N-Amino Side Chains as prepared in Example 35

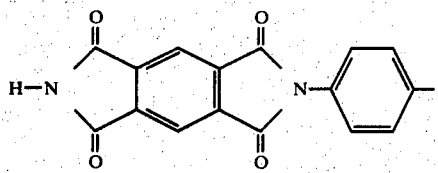

| Amine Reactant | Pyromellitic Diimide Product | m.p. °C. |
|---|---|---|
| Unsym. Dimethylhydrazine | N-(dimethylamino) | 293–295 |
| Acethydrazide | N-(acetylamino) | 293–294.5 |
| Propionic Acid Hydrazide | N-(propionylamino) | |
| Butyric Acid Hydrazide | N-(butyrolamino) | |
| Benzoic Acid Hydrazide | N-(benzoylamino) | 313–314.5 |
| Ethyl Carbazate | N-(carbethoxyamino) | 244–245 |
| Tert. Butyl Carbazate | N-(t-butoxycarbonyl-amino) | 133–134 |

EXAMPLE 36

N-Methyl-N'-Hydroxymethyl pyromellitic diimide

N-methyl pyromellitic diimide, 2.30 g. (10 mmole), is added with vigorous stirring at room temperature (23° C.) to a solution of 36% formaldehyde, 5 ml., in 30 ml. of water under nitrogen followed by the addition of 10 drops of 2.5 N sodium hydroxide. The mixture is heated at 95° for 6 hours and then cooled in ice. The insolubles are collected, rinsed with cold water, ethyl ether and dried furnishing 1.98 g. of N-methyl-N'-hydroxymethyl pyromellitic diimide, m.p. >300° C.

TABLE X

Unsymmetrical N,N'-Disubstituted Pyromellitic Diimides with N'-Hydroxymethyl Side Chains as prepared in Example 36

![Structure: R—N(pyromellitic diimide)N—CH2OH]

| Pyromellitic Diimide Reactant | Pyromellitic Diimide Product (R) | m.p. °C. |
|---|---|---|
| N-Methyl | N-Methyl-N'-hydroxymethyl | >300 |
| N-Ethyl | N-Ethyl-N'-hydroxymethyl | >300 |
| N-(n-Propyl) | N-(n-propyl)-N'-hydroxymethyl | |
| N-(n-Butyl) | N-(n-butyl)-N'-hydroxymethyl | |
| N-Benzyl | N-Benzyl-N'-hydroxymethyl | 284–285 |
| N-(2-Hydroxyethyl) | N-(2-Hydroxyethyl)-N'-hydroxymethyl | 273–274 |
| N-(3-Hydroxyprop-1-yl) | N-(3-Hydroxyprop-1-yl)-N'-hydroxymethyl | |

EXAMPLE 37

N-(2-Hydroxyethyl)-N'-methyl pyromellitic diimide

To a solution of ethanolamine 1.32 ml. (22 mmole), in 20 ml. of dimethylformamide is added with stirring at room temperature under nitrogen 4.62 g. (20 mmole) of N-methyl pyromellitic imide anhydride. The mixture is stirred at room temperature for 30 minutes, at 50° C. for 30 minutes, at 100° C. for 30 minutes and at 150° C. for 1 hours, and then is cooled and diluted with 80 ml. of ethanol. The crystals are collected, rinsed with cold ethanol and ethyl ether and dried furnishing 4.3 g. of N-(2-hydroxyethyl)-N'-methyl pyromellitic diimide, m.p. 272°–4° C.

TABLE XI

Unsymmetrical N,N'-Disubstituted Pyromellitic Diimides with N-Hydroxyalkyl-N'-Methyl Side Chains as prepared in Example 37

![Structure: CH3N(pyromellitic diimide)N—R]

| Amine Reactant | N'-Methyl Pyromellitic Diimide Product (R) | M.p. °C. |
|---|---|---|
| Ethanolamine | N-(2-Hydroxyethyl) | 272–274 |
| 3-Amino-1-propanol | N-(3-Hydroxyprop-1-yl) | 235–236 |
| 4-Amino-1-butanol | N-(4-Hydroxybut-1-yl) | |
| 2-Amino-1-butanol | N-(1-Hydroxybut-2-yl) | |

What is claimed is:

1. A compound having the formula:

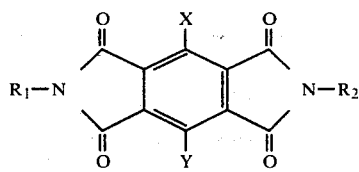

wherein $R_1$ is hydrogen and $R_2$ is loweralkyl, loweralkenyl, loweralkynyl, cycloalkyl, loweralkanoyl, benzoyl, substituted phenyl wherein the substituent is sulfonamido, hydroxy, carboxy, nitro, methylthio, or hydroxy loweralkyl; substituted loweralkyl wherein the substituents are one or two of hydroxy, halogen nitro, loweralkoxy, carboxy, phenyl, hydroxyloweralkoxy, loweralkanoyloxy, phenoxy, amino, mono- or di-loweralkylamino, mercapto, loweralkylthio, loweralkylsulfinyl, loweralkylsulfonyl, loweralkoxycarbonyl, carbamyl, hydroxyloweralkylthio, hydroxyloweralkylsulfinyl, hydroxyloweralkylsulfonyl, hydroxyloweralkylamino, di-(hydroxyloweralkyl)amino, loweralkanoylamino or hydroxyphenyl; diloweralkylamino, or mono-substituted amino wherein the substituent is loweralkanoyl, benzoyl or loweralkoxycarbonyl; and X and Y are independently hydrogen, loweralkyl or halogen.

2. The compound of claim 1 wherein $R_2$ is, loweralkyl, loweralkenyl, substituted loweralkyl wherein the substituent is one or two of hydroxy, amino, mono- or di-loweralkylamino, loweralkoxy, carboxy, carbamyl, phenyl, hydroxyloweralkoxy, hydroxyloweralkylthio, loweralkanoyloxy, mercapto, loweralkylthio, loweralkylsulfinyl, loweralkylsulfonyl, loweralkoxycarbonyl; loweralkanoyl, diloweralkylamino, benzoylamino; and X and y are hydrogen.

3. The compound of claim 2 wherein $R_2$ is, loweralkyl, loweralkenyl, substituted loweralkyl, wherein the substituent is one of hydroxy, or loweralkanoyloxy; loweralkylthio, loweralkylsulfinyl, loweralkylsulfonyl, hydroxyloweralkylthio, hydroxyloweralkoxy; loweralkanoyl or diloweralkylamino.

4. The compound of claim 3 wherein $R_2$ is, loweralkyl, substituted loweralkyl wherein the substituent is one of hydroxy, hydroxyloweralkoxy, or hydroxyloweralkylthio.

5. The compound of claim 1 which is N-methyl pyromellitic diimide.

6. The compound of claim 1 which is N-(2-hydroxyethyl)pyromellitic diimide.

7. The compound of claim 1 which is N-[2-(2-hydroxyethylthio)ethyl]pyromellitic diimide.

8. The compound of claim 1 which is N-[2-(2-hydroxyethoxy)ethyl]pyromellitic diimide.

9. The compound of claim 1 which is N-[2-(methylthio)ethyl]pyromellitic diimide.

10. The compound of claim 1 which is N-[2-(methylsulfinyl)ethyl]pyromellitic diimide.

11. The compound of claim 1 which is [2-(methylsulfonyl)ethyl]pyromellitic diimide.

12. A method for increasing the feed efficiency of a ruminant animal which comprises orally administering to said ruminant animal an effective amount of a compound of claim 1.

13. A composition useful for increasing the feed efficiency of ruminant animals which comprises an inert carrier and an effective amount of a compound of claim 1.

* * * * *